US010589433B2

(12) United States Patent
Al Nahwi et al.

(10) Patent No.: US 10,589,433 B2
(45) Date of Patent: *Mar. 17, 2020

(54) UNDERWATER PIPELINE INSPECTION CRAWLER

(71) Applicant: Saudi Arabian Oil Company, Dhahran (SA)

(72) Inventors: Ammar Al Nahwi, Dhahran (SA); Fadl Abdellatif, Thuwal (SA); Ali Outa, Thuwal (SA); Ihsan Al-Taie, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 140 days.

This patent is subject to a terminal disclaimer.

(21) Appl. No.: 15/677,575

(22) Filed: Aug. 15, 2017

(65) Prior Publication Data

US 2018/0080905 A1 Mar. 22, 2018

Related U.S. Application Data

(60) Provisional application No. 62/397,175, filed on Sep. 20, 2016.

(51) Int. Cl.
*B08B 9/023* (2006.01)
*G01B 17/02* (2006.01)
(Continued)

(52) U.S. Cl.
CPC ............ *B25J 15/0028* (2013.01); *B08B 1/00* (2013.01); *B08B 3/024* (2013.01); *B08B 9/023* (2013.01);
(Continued)

(58) Field of Classification Search
CPC ........ B25J 15/0028; B08B 1/00; B08B 3/024; B08B 9/023; G01N 23/04; G01N 23/18;
(Continued)

(56) References Cited

U.S. PATENT DOCUMENTS 4,290,123 A 9/1981 Pickens
5,698,854 A * 12/1997 Gupta .................... G01N 23/18
250/358.1
(Continued)

FOREIGN PATENT DOCUMENTS

EP 0000808 A1 2/1979

OTHER PUBLICATIONS

International Preliminary Report on Patentability for International Patent Application No. PCT/US2017/049011 dated Aug. 23, 2018. 13 pages.
(Continued)

*Primary Examiner* — Helen C Kwok
(74) *Attorney, Agent, or Firm* — Leason Ellis LLP

(57) ABSTRACT

An inspection crawler, and systems and methods for inspecting underwater pipelines are provided. The system includes the inspection crawler having a housing with a first side, an opposing second side, a power source, and a controller. The crawler includes an inspection tool, at least two pairs of latching arms, each latching arm including a rolling element, and at least two pairs of driving wheels. The system also includes at least one communication unit configured to communicate with the inspection crawler and to communicate aerially with one or more remote devices and, and at one sea surface unit. The inspection crawler can further include a connecting structure connecting the front and back portions of the crawler, and configured to elongate and shorten the inspection crawler.

11 Claims, 14 Drawing Sheets

(51) Int. Cl.

| | | |
|---|---|---|
| *G01N 29/22* | (2006.01) | |
| *G01N 29/04* | (2006.01) | |
| *B25J 15/00* | (2006.01) | |
| *B08B 1/00* | (2006.01) | |
| *B08B 3/02* | (2006.01) | |
| *B63C 11/52* | (2006.01) | |
| *F16L 1/26* | (2006.01) | |
| *B63G 8/00* | (2006.01) | |
| *B63H 19/08* | (2006.01) | |
| *F16H 19/08* | (2006.01) | |
| *B63G 8/14* | (2006.01) | |
| *B23K 31/12* | (2006.01) | |
| *B63G 8/42* | (2006.01) | |
| *B25J 9/00* | (2006.01) | |
| *B63C 11/42* | (2006.01) | |
| *E21B 41/04* | (2006.01) | |
| *F16H 35/18* | (2006.01) | |
| *F16H 1/22* | (2006.01) | |
| *F16L 55/00* | (2006.01) | |
| *B62D 57/00* | (2006.01) | |
| *F16H 1/16* | (2006.01) | |
| *F16H 37/04* | (2006.01) | |

(52) U.S. Cl.
CPC ............ *B23K 31/125* (2013.01); *B25J 9/0009* (2013.01); *B25J 15/0009* (2013.01); *B63C 11/42* (2013.01); *B63C 11/52* (2013.01); *B63G 8/001* (2013.01); *B63G 8/14* (2013.01); *B63G 8/42* (2013.01); *B63H 19/08* (2013.01); *E21B 41/04* (2013.01); *F16H 19/08* (2013.01); *F16H 35/18* (2013.01); *F16L 1/26* (2013.01); *F16L 1/265* (2013.01); *G01B 17/02* (2013.01); *G01N 29/04* (2013.01); *G01N 29/225* (2013.01); *B62D 57/00* (2013.01); *B63G 8/00* (2013.01); *B63G 2008/002* (2013.01); *B63G 2008/005* (2013.01); *B63G 2008/008* (2013.01); *F16H 1/16* (2013.01); *F16H 1/222* (2013.01); *F16H 37/041* (2013.01); *F16H 2019/085* (2013.01); *F16L 55/00* (2013.01); *G01N 2291/0234* (2013.01); *G01N 2291/02854* (2013.01); *G01N 2291/2675* (2013.01)

(58) Field of Classification Search
CPC . G01N 29/225; G01N 29/2412; G01N 29/265
See application file for complete search history.

(56) References Cited

U.S. PATENT DOCUMENTS

| | | | | |
|---|---|---|---|---|
| 7,594,448 | B2* | 9/2009 | Jacobson | G05D 1/0891 |
| | | | | 73/865.8 |
| 7,656,997 | B1* | 2/2010 | Anjelly | G01N 23/04 |
| | | | | 378/59 |
| 8,185,241 | B2* | 5/2012 | Jacobsen | B62D 55/0655 |
| | | | | 700/1 |
| 8,695,524 | B2* | 4/2014 | Tilley | B08B 17/02 |
| | | | | 114/312 |
| 9,239,297 | B2* | 1/2016 | Sibai | B25J 5/007 |
| 9,400,263 | B2* | 7/2016 | An | G01N 29/225 |
| 9,874,507 | B2* | 1/2018 | Dingman | G01N 23/12 |
| 2007/0276552 | A1* | 12/2007 | Gupta | G01N 23/18 |
| | | | | 250/358.1 |
| 2009/0120215 | A1* | 5/2009 | Jacobson | G05D 1/0891 |
| | | | | 73/865.8 |
| 2010/0212574 | A1* | 8/2010 | Hawkes | B63C 11/42 |
| | | | | 114/328 |
| 2010/0235018 | A1* | 9/2010 | Christ | G01N 21/952 |
| | | | | 701/2 |
| 2014/0146161 | A1* | 5/2014 | Sibai | B25J 5/007 |
| | | | | 348/84 |
| 2014/0260705 | A1* | 9/2014 | Kimpel, Jr. | G01M 99/00 |
| | | | | 73/865.8 |
| 2014/0338472 | A1* | 11/2014 | Chang | G21C 17/017 |
| | | | | 73/865.8 |
| 2015/0153170 | A1* | 6/2015 | Gonzalez | G01B 21/22 |
| | | | | 701/300 |
| 2016/0059939 | A1* | 3/2016 | Lamonby | B08B 9/023 |
| | | | | 114/337 |
| 2016/0272291 | A1* | 9/2016 | Outa | B60F 3/0015 |
| 2018/0080904 | A1* | 3/2018 | Al Nahwi | F16L 1/265 |
| 2018/0080905 | A1* | 3/2018 | Al Nahwi | B08B 1/00 |
| 2018/0208283 | A1* | 7/2018 | Munro | B63C 11/52 |

OTHER PUBLICATIONS

No Author. "Epic TM Riser Repair Clamp." 4subsea. No date. https://www.4subsea.com/wp-content/uploads/2017/03/Product-Sheet-EPIC_FLEX_I.3.17.D.pdf. 2 pages.
No Author. "Flexible Riser Inspection." Innospection—Advanced Inspection Solutions. Innospection Ltd, 2016. Web. Aug. 14, 2017. <http://www.innospection.com/services/flexiblerisers>. 2 pages.
International Search Report and Written Opinion for International Patent Application No. PCT/US2017/049011 dated Dec. 14, 2017. 16 pages.

\* cited by examiner

UNDERWATER PIPELINE INSPECTION CRAWLER

CROSS-REFERENCE TO RELATED APPLICATION

The present invention claims priority to U.S. patent application Ser. No. 62/397,175, filed Sep. 20, 2016, which is hereby incorporated by reference in its entirety.

FIELD OF THE INVENTION

The present invention relates to underwater robots and methods and systems for inspection of underwater pipelines.

BACKGROUND OF THE INVENTION

Underwater pipelines can include a concrete weight coating to ensure their stability on the seabed. Segments of pipelines are generally welded together creating weld joints between the segments. The weld joints, however, do not have concrete coating, and thus are either exposed to the environment or have some kind of wire mesh or guard to protect them from outside damage. As such, the weld joints are generally more vulnerable to deterioration and leaks (e.g., due to corrosion) and thus require frequent inspection. The cross-sectional diameter of the weld joints is also typically smaller than the concrete coated segments of the pipeline.

Due in part to the configuration of the underwater pipelines (e.g., weld joints), external inspection of underwater pipelines can be a challenging task. Remotely operated vehicles (ROVs) have been used to inspect these pipelines by taking inspection readings at targeted spots along the pipeline. These external inspections, however, become even more difficult when the pipeline starts from shore and transitions into a shallow zone of water, where the shallow water's high currents make it difficult for ROVs to access the pipeline and, particularly, the weld joints.

As such, there is a need for new approaches to inspecting underwater pipelines. The present invention addresses these and other limitations associated with conventional inspection protocols for underwater pipelines.

SUMMARY OF THE INVENTION

According to an aspect of the present invention, a system for inspection of an underwater pipeline is provided. The system includes at least one inspection crawler configured to move along the underwater pipeline and traverse weld joints connecting portions of the underwater pipeline. The at least one inspection crawler comprises a housing, a power source, a controller, at least one inspection tool, at least two pairs of latching arms each having a rolling element, at least two pairs of driving wheels. The system further includes at least one communication unit located on top of the surface of the water and operatively connected to the at least one inspection crawler. The at least one communication unit is configured to communicate aerially with one or more remote devices and communicate with the at least one inspection crawler via a tether. The system further includes at least one sea surface unit operatively connected to the at least one communication unit.

According to another aspect, the at least one communication unit is configured to float on the surface of the water. According to another aspect, the at least one sea surface unit is configured to control operations of the at least one inspection crawler via control signals. According to another aspect, the system further includes at least one remotely operated vehicle (ROV), where the inspection crawler is configured to operate as a docking station for the ROV. The ROV is configured to assist the inspection crawler in underwater navigation when the ROV is docked in the inspection crawler.

According to another aspect, each of the inspection crawler, communication unit, and sea surface unit include at least one transmitter and at least one receiver, and the transmitters and receivers are configured to transmit and receive, respectively, data and control signals.

According to another aspect, the rolling elements of the inspection crawler are omni-wheels.

According to another aspect, the housing of the inspection crawler further comprises a front portion and a back portion and a connecting structure connecting the front portion and the back portion. The connecting structure comprises an extendable and contractable member that is operable to elongate and shorten, respectively, the length of the inspection crawler.

According to another aspect, the at least two pairs of latching arms each include a joint that divides each latching arm into an upper segment and a lower segment. The joints enable the latching arms to accommodate pipelines of varying diameters.

According to another aspect, the inspection crawler further includes a pneumatic actuator operatively connected to the housing and the latching arms. The pneumatic actuator configures the latching arms to selectively hug the surface of the pipeline.

According to another aspect, the inspect crawler includes an electric actuation mechanism operatively connected to the housing and the latching arms, such that the electric actuation mechanism configures the latching arms to selectively hug the surface of the pipeline.

According to yet another aspect of the present invention, a method for traversing a weld joint along a surface of an underwater pipeline with the inspection crawler is provided. In accordance with the method, the inspection crawler is parked at a location proximate to the weld joint, and to park the inspection crawler, the rolling elements of the at least two pairs of latching arms are pressed against the surface of the pipeline such that the rolling elements of the front pair of latching arms are substantially aligned with the rolling elements of the rear pair of latching arms. The rolling elements of the front pair of latching arms are then lifted from the surface of the pipeline, and a front portion of the inspection crawler is propelled across the weld joint using the driving wheels. The rolling elements of the front pair of latching arms are then lowered to contact the surface of the pipeline and the rolling elements of the rear pair of latching arms are lifted from the surface of the pipeline. A back portion of the inspection crawler is then propelled across the weld joint using the driving wheels, and the rolling elements of the rear pair of latching arms are lowered to contact the surface of the pipeline.

According to another aspect of the present invention, a method for traversing a weld joint with the inspection crawler having the connecting structure is provided. In accordance with the method, the inspection crawler is parked at a location proximate to the weld joint, and to park the inspection crawler, the rolling elements of the at least two pairs of latching arms are pressed against the surface of the pipeline such that the rolling elements of the front pair of latching arms are substantially aligned with the rolling elements of the rear pair of latching arms. The connecting structure is then extended to propel a first portion of the inspection crawler over the weld joint. Then, the connecting structure is contracted to propel a second portion of the inspection crawler over the weld joint.

These and other aspects, features, and advantages can be appreciated from the following description of certain embodiments of the invention and the accompanying drawing figures and claims.

DETAILED DESCRIPTION CERTAIN OF EMBODIMENTS OF THE INVENTION

Figure 1:
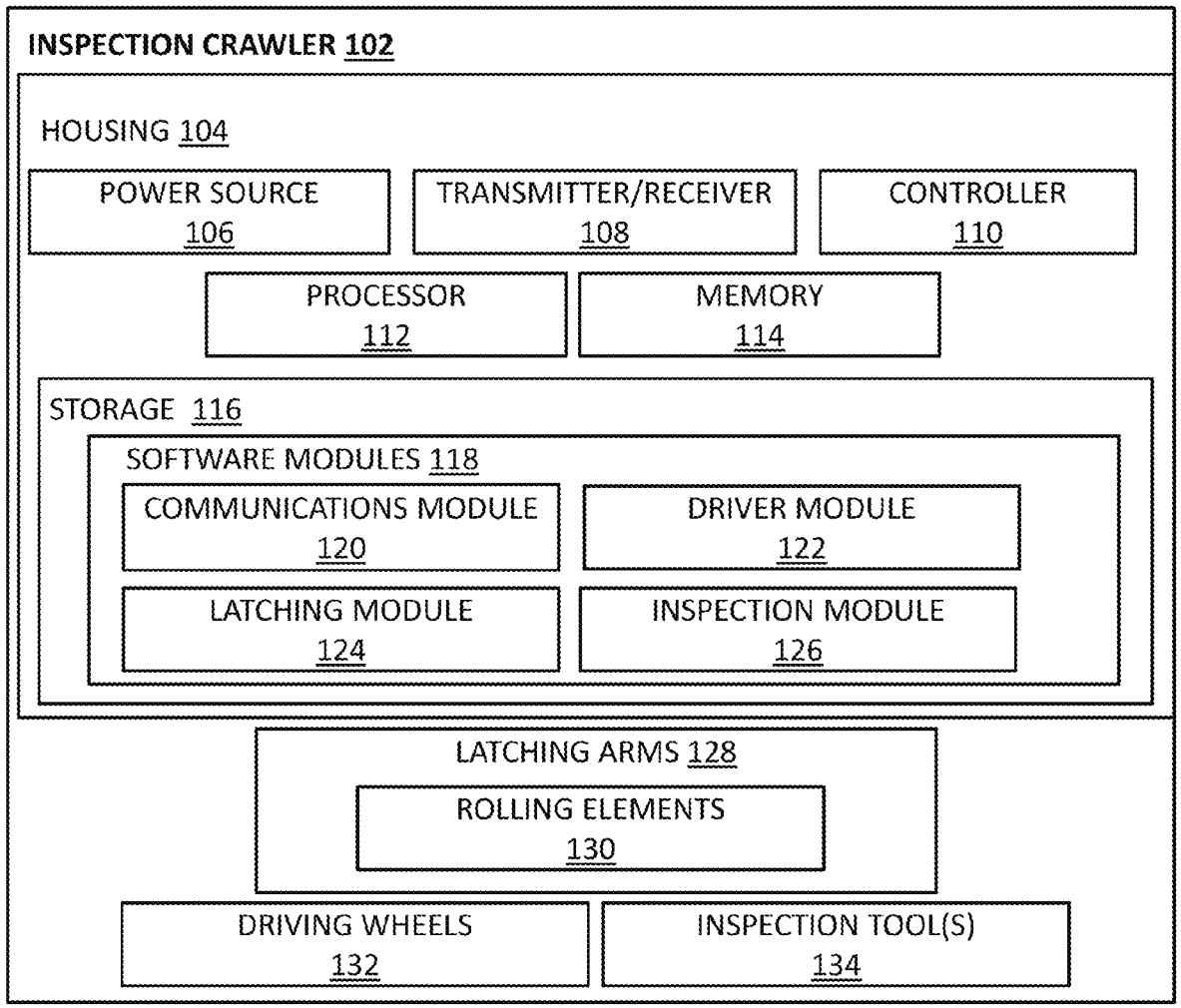
FIG. 1 is a block diagram illustrating an example configuration of an underwater crawler according to at least one embodiment of the present application.

The present application details an underwater inspection crawler, and systems and methods for inspection of underwater pipelines. In particular, the invention is described in connection with several embodiments of an underwater inspection crawler capable of traversing an underwater pipeline and conducting inspections on the pipeline. The underwater inspection crawler of the present application targets, among other things, the challenge of crossing weld joints along an underwater pipeline, and stabilizing the crawler on the pipeline. Further, the inspection crawler ensures upward position of the crawler on top of the underwater pipeline by rectifying it against underwater currents, gravity, and discontinuities along the pipelines.

In one or more embodiments, the underwater inspection crawler comprises a housing containing a power source and a controller. In one or more embodiments, the underwater crawler can also comprise at least one inspection tool operatively connected to the housing. The crawler can also include at least two pairs of latching arms operatively connect to the housing. Each latching arm comprises a rolling element attached to the distal portion of each latching arm, the rolling elements being configured to selectively maintain contact with the surface of the pipeline via tension to prevent detachment of the inspection crawler from the surface of the pipeline. The crawler can also comprise at least two pair of driving wheels attached to a bottom portion of the housing, the driving wheels being configured to propel the inspection crawler across the surface of the pipeline.

In one or more embodiments, embodiments of systems and methods for inspection of an underwater pipeline using the crawler are provided. In particular, the system can comprise at least one underwater crawler, and at least one communication unit located on top of the surface of the water and tethered to the inspection crawler. The communication unit can communicate aerially with one or more remote computing devices, and can communicate with the crawler via the tether. The communication unit can also be connected to a support vessel or a sea surface robotic vehicle via a tether or, alternatively, via an underwater wireless connection (e.g., acoustics, laser, visible LED light, radio frequency [RF]).

The present systems provide several advantages over previous underwater pipeline inspection systems. For example, the inspection crawler of the present application provides effective propulsion along an underwater pipeline via the driving wheels, and maintains stability along the pipeline via the latching arms of the inspection crawler. These advantages are particularly distinct for moving along underwater horizontal pipelines having a concrete weight coat around its steel wall and seafloor sand underneath them. The inspection crawler of the present application is also easily deployed on an underwater pipeline that begins offshore. This feature provides the inspection crawler with a distinct advantage over swimming robots in shallow waters, as swimming robots have difficulty finding pipelines in shallow water due to low visibility. Further, unlike swimming robots, the inspection crawler of the present application does not need buoyancy control for stable inspection measurements. The present inspection crawler also allows for novel, effective movement across the weld joints of the underwater pipeline.

The referenced underwater inspection crawlers, and systems and methods for underwater pipeline inspection are now described more fully with reference to the accompanying drawings, in which one or more illustrated embodiments and/or arrangements of the systems and methods are shown. The systems and methods of the present application are not limited in any way to the illustrated embodiments and/or arrangements as the illustrated embodiments and/or arrangements are merely exemplary of the systems and methods, which can be embodied in various forms as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods.

Inspection Crawler

FIG. 1 displays a block diagram illustrating an example configuration of an underwater inspection crawler according to at least one embodiment of the present application. With reference to FIG. 1, in accordance with one or more embodiments, the underwater inspection crawler 102 comprises a housing 104. The housing 104 includes a power source 106, at least one transmitter/receiver 108, and a controller 110. In one or more embodiments, the at least one transmitter/receiver 108 is configured to transmit and receive signals (e.g., control signals), as well as for transmit and receive data. In one or more embodiments, the at least one transmitter-receiver can be a transceiver or can be a separate transmitter and a separate receiver. In one or more embodiments, a tether can be attached to the inspection crawler 102 for communication with one or more remote devices in place of or in addition to the transmitter/receiver 108. The controller 110 can be arranged with various hardware and software components that serve to enable various operations of the inspection crawler 102, including a hardware processor 112, a memory 114, and storage 116. The processor 112 serves to execute software instructions that can be loaded into the memory 114. The processor 112 can comprise a number of processors, a multi-processor core, or some other type of processor, depending on the particular implementation.

Preferably, the memory 114 and/or the storage 116 are accessible by the processor 112, thereby enabling the processor 112 to receive and execute instructions stored on the memory 114 and/or on the storage 116. The memory 114 can be, for example, a random access memory (RAM) or any other suitable volatile or non-volatile computer readable storage medium. In addition, the memory 114 can be fixed or removable. The storage 116 can take various forms, depending on the particular implementation. For example, the storage 116 can contain one or more components or devices such as a hard drive, a flash memory, a rewritable optical disk, a rewritable magnetic tape, or some combination of the above. The storage 116 also can be fixed or removable.

In one or more embodiments, one or more software modules 118 are encoded in the storage 116 and/or in the memory 114. The software modules can comprise one or more software programs or applications having computer program code or a set of instructions executed in the processor 112. Such computer program code or instructions for carrying out operations and implementing aspects of the systems and methods disclosed herein can be written in any combination of one or more programming languages. The program code can execute entirely on the inspection crawler 102, as a stand-alone software package, partly on the inspection crawler 102 and partly on a remote computer/device or entirely on such remote computers/devices. In the latter scenario, the remote computer systems can be connected to the inspection crawler 102 through any type of network, including a local area network (LAN) or a wide area network (WAN), or the connection can be made through an external computer (for example, through the Internet using an Internet Service Provider).

In one or more embodiments, included among the software modules 118 can be a communications module 120, and a driver module 122, a latching module 124, and/or an inspection module 126 that are executed by processor 112. During execution of the software modules 118, the processor 110 is configured to perform various operations relating to the configuration of the inspection crawler 102. In addition, it should be noted that other information and/or data relevant to the operation of the present systems and methods can also be stored on the storage 130, for instance various control programs used in the configuration of the inspection crawler 102.

Similarly, in an alternative embodiment, the inspection crawler 102 can include a control module (in place of controller 110) that can be arranged with various hardware and software components that serve to enable operation of the system, including a processor, a memory, a communications module, a driver module, a latching module, and/or an inspection module, and a computer readable storage medium in order to execute the various functions of the inspection crawler.

In one or more embodiments, the inspection crawler 102 further includes at least two pairs of latching arms 128 operatively connected to the housing to the housing 104 (e.g., via spring-loaded active joints). In one or more implementations (e.g., FIG. 3A), the two pairs of latching arms 128 can comprise a front pair and a rear pair. The first latching arm of each of the front pair and the rear pair extends from a first side of the housing, and a second latching arm of each of the front pair and the rear pair extends from a second, opposing side of the housing. The latching arms 128 each include a rolling element 130 at its distal end, which are configured to selectively maintain contact with a surface of the pipeline via tension to prevent detachment of the inspection crawler 102 from the surface of the underwater pipeline. In one or more embodiments, the inspection crawler 102 further includes at least two pairs of driving wheels 132 attached to a bottom portion of the housing 104. In one or more implementations, the driving wheels 132 are configured to propel the inspection crawler 102 across the surface of the pipeline.

In one or more embodiments, the inspection crawler 102 further comprises one or more inspection tools 134 operatively connected to the housing. In one or more embodiments, at least one inspection tool 134 can comprise an inspection probe for collecting data related to the inspection of the underwater pipeline, as discussed in greater detail below. The movement of the inspection tools is controlled by the controller 110 via instructions implemented by the inspection module 126.

Underwater Pipeline Inspection System

Figure 2:
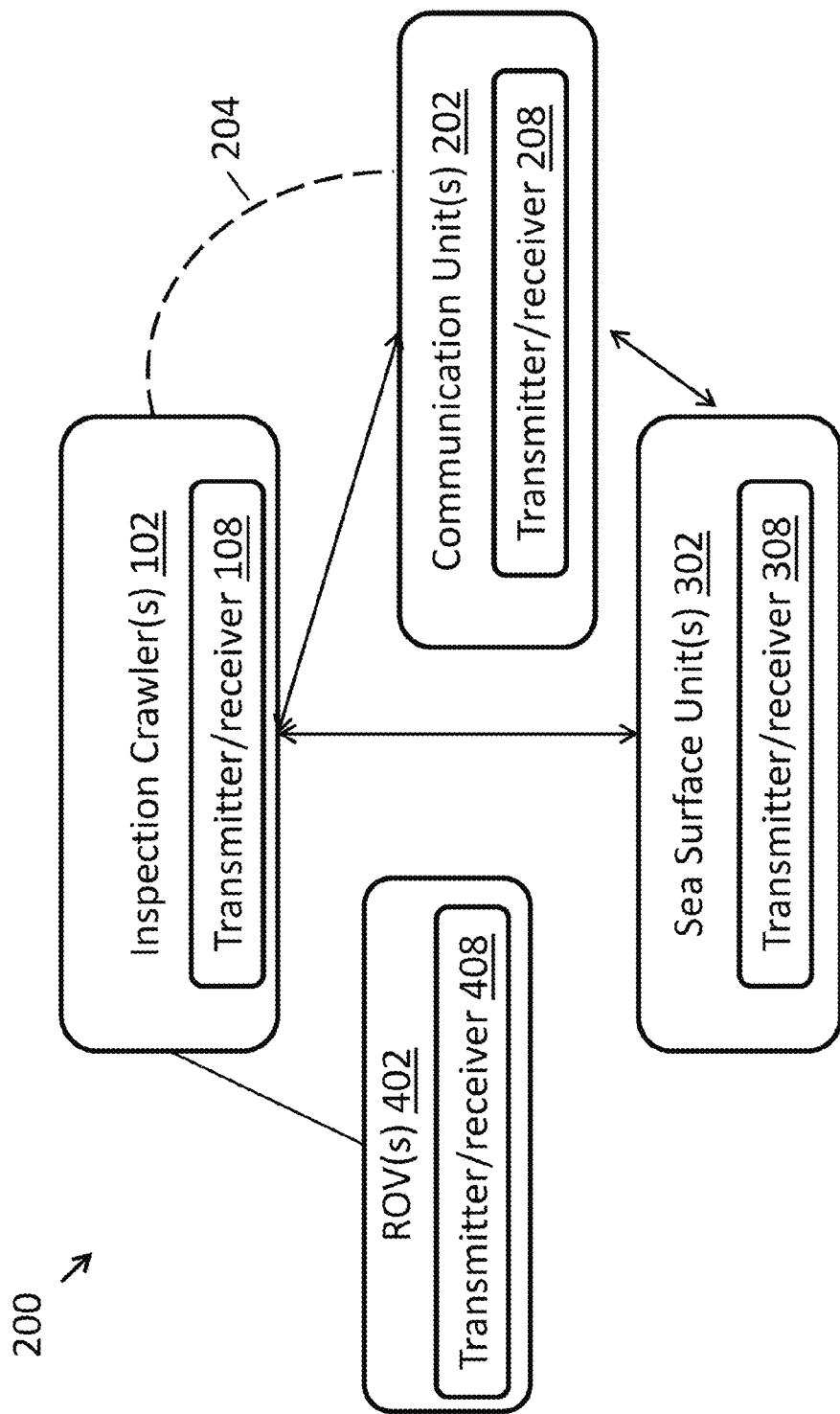
FIG. 2 is a diagram of an example system for underwater pipeline inspection according to at least one embodiment of the present application.

FIG. 2 illustrates an exemplary system 200 for underwater pipeline inspection according to at least one embodiment of the present application. The system 200 can include one or more inspection crawlers 102, one or more communication units 202, and one or more sea surface units 302. Each of the inspection crawler 102, communication unit 202, and sea surface unit 302 can comprise at least one transmitter/receiver, and wherein the transmitters and receivers are configured to transmit and receive, respectively, data and control signals, transmitted between the inspection crawler 102, communication unit 202, and sea surface unit 302, as discussed in greater detail below.

In one or more embodiments, the communication unit 202 is located on top of the surface of the water and operative connected to the inspection crawler 102, via a tether 204 for example. The communication unit 202 is configured to communicate aerially with one or more remote devices and to communicate with the inspection crawler 102 (e.g., via the tether 204). For example, in at least one implementation, the communication unit 202 can float on the surface of the water (e.g., a buoy). In one or more embodiments, the communication unit 202 can comprise at least one transmitter/receiver 208 for transmitting and receiving signals (e.g., control signals), as well as for transmitting and receiving data. In one or more embodiments, the one or more transmitter-receivers can be transceivers or can be separate transmitters and receivers.

In one or more embodiments, the sea surface unit 302 is operatively connected to the communication unit 202. In one or more embodiments, the sea surface unit 302 can be any number of different types of sea surface vehicles, including but not limited to a boat, a sea surface robotic vehicle, or a control station in a support vessel. One example of a suitable sea surface robotic vehicle is described in U.S. application Ser. No. 15/069,631, filed on Mar. 14, 2016, entitled "Water Environment Mobile Robots," which is hereby incorporated by reference as if set forth in its entirety herein. In an embodiment in which the surface unit 302 is a control center, the control center (302) can be configured to control operation of the inspection crawler 102 and/or the communication unit 202 using control signals that are communicated between the control center (302) and the inspection crawler 102 and/or communication unit 202. In certain embodiments, the control signals transmitted from the control center 302 to control the operations of the inspection crawler 102 can be relayed to the inspection crawler 102 via the communication unit 202. The control center (302) can include at least one transmitter-receiver 308 for transmitting and receiving signals (e.g., control signals), as well as for transmitting and receiving data. In one or more embodiments, the one or more transmitter-receivers can be transceivers or can be separate transmitters and receivers.

In an embodiment in which the sea surface unit is 302 comprises a control center, the control center can include one or more computing devices, which can have the same or similar operations and features as the controller 110 as described above. For example, the one or more computing devices of the control center can have various hardware and software components that serve to enable various operations of the control center, inspection crawler(s) 102, and/or communication unit(s) 202. These various hardware and software components can comprise one or more hardware processors, and a memory and/or storage accessible by the processor. The processor serves to execute software instructions that can be loaded into the memory/storage. More specifically, one or more software modules can be encoded in the storage and/or in the memory. The software modules can comprise one or more software programs or applications having computer program code or a set of instructions executed in the processor. In certain embodiments, the control center 302 can also include a joystick or other mechanism for controlling the movement and operations of the inspection crawler(s) 102 and/or the communication unit(s) 202.

In one or more embodiments, the system of the present application can further comprise at least one swimming remotely operative vehicle (ROV) 402 that is configured to dock into the crawler 102, or alternatively, is connected to the crawler 102 for improved environment perception and collaborative work (e.g., inspection tasks). More particularly, in one or more embodiments, the crawler 102 can act as a docking station for a deployable inspection ROV 402 that is powered and controlled via a tether connected to it. For example, such an ROV can help navigate or guide the way of the crawler by swimming and searching for the pipe in areas along the pipeline where the pipe is buried under the seabed. With the help of the ROV 402, the crawler 102 can navigate on the seabed until it finds the buried pipe again. In one or more embodiments, the ROV 402 can further comprise one or more computing devices, which can have the same or similar operations as the controller 110 as discussed above. In at least one embodiment, the ROV 402 can further comprise a transmitter/receiver 408.

Inspection Crawler Attachment and Movement Along Underwater Pipeline

Figure 3A:
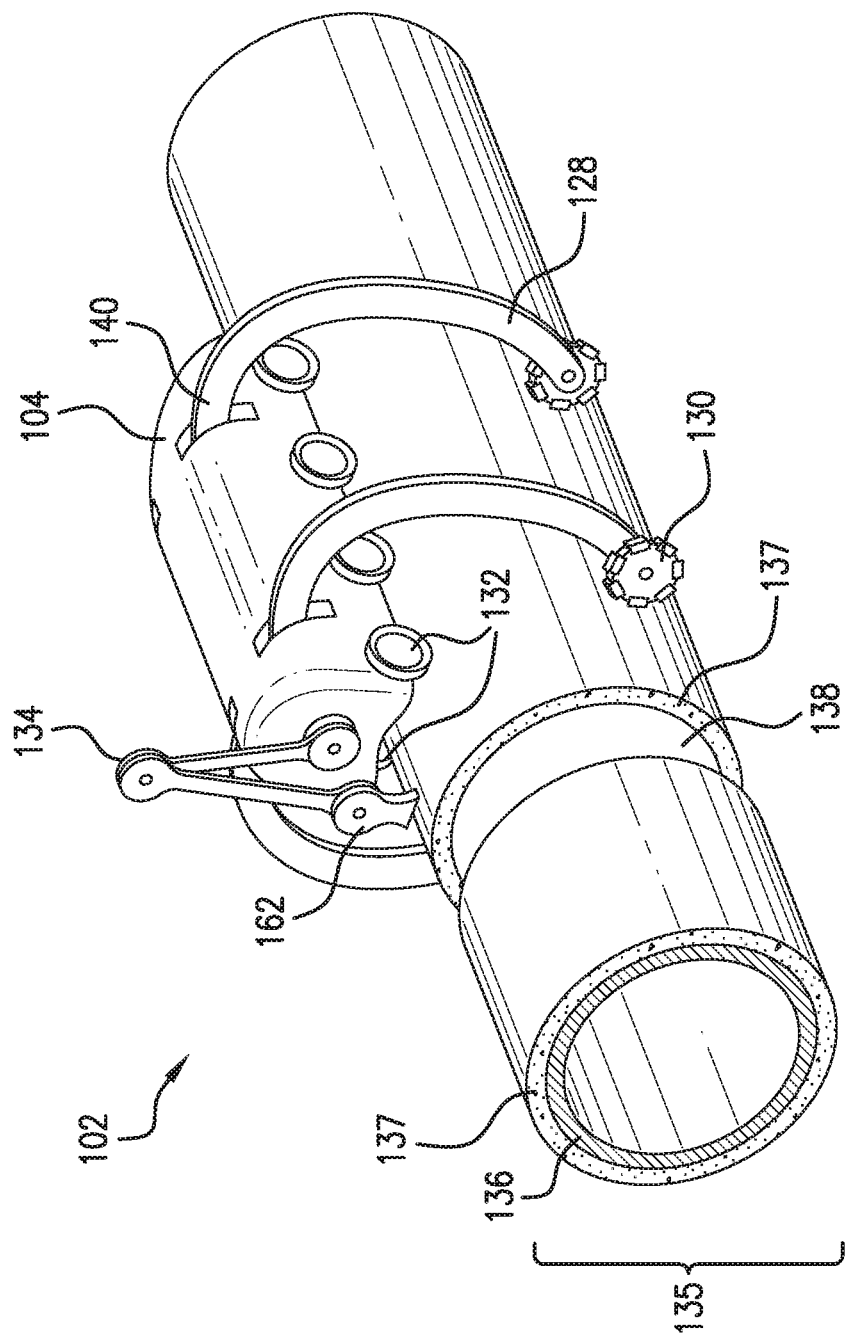
FIGS. 3A-B illustrate the attachment of the underwater crawler to an underwater pipeline (3A, prospective view; 3B, front view) according to at least one embodiment of the present application.
Figure 3B:
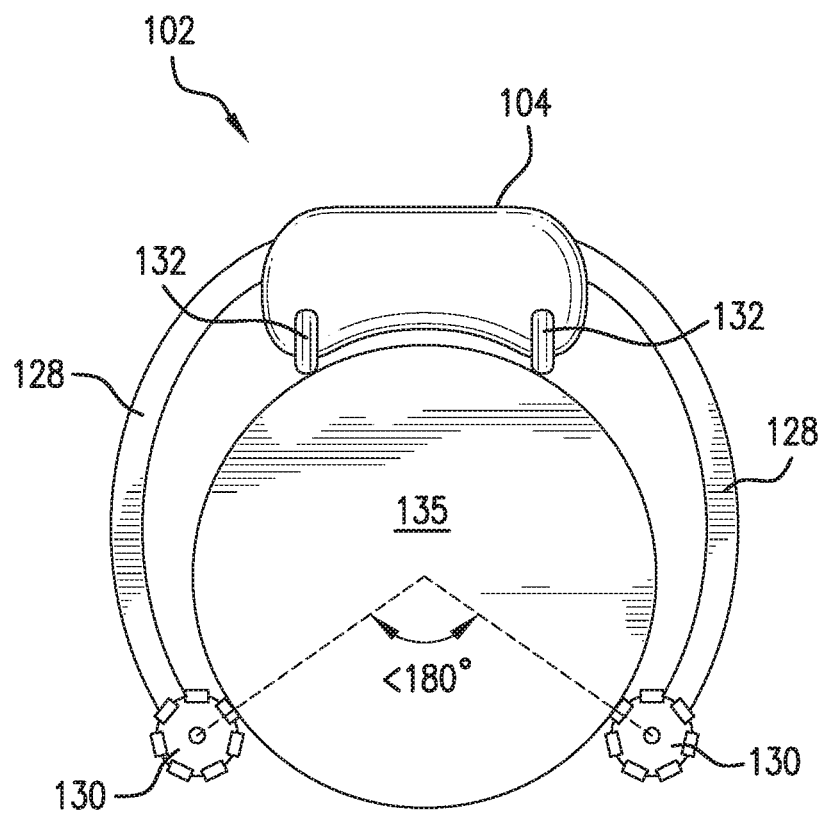

FIGS. 3A and 3B illustrate the attachment of the underwater crawler to an underwater pipeline according to at least one embodiment. With reference to FIGS. 3A-B, in one or more embodiments, the inspection crawler 102 is configured to crawl along the underwater pipeline having numerous segments of pipes 135. The pipes 135 can each comprise a steel wall 136 as the inner layer of the pipe, and a concrete weight coat 137 as an outer layer of the pipe onto which the crawler 102 attaches. The segments of pipes 135 are generally welded together creating weld joints 138 between the segments. The weld joints 138, however, do not have concrete coating, and thus are either exposed to the environment or have some kind of wire mesh or guard to protect them from outside damage.

With continued reference to FIGS. 3A and 3B, the inspection crawler 102 comprises a housing 104 and at least two pairs of latching arms 128. As shown in FIGS. 3A and 3B, in one or more embodiments, the latching arms 128 have a curved shape. In one or more embodiments, each latching arm 128 is operatively connected to the housing via a spring-loaded active joint 140. The latching arms 128 each include a rolling element 130 attached at its distal end. The rolling elements 130 are configured to selectively maintain contact with a surface of the pipeline via tension to prevent detachment of the inspection crawler 102 from the surface of the pipeline. In at least one embodiment, and as shown in FIGS. 3A and 3B, the rolling elements 130 are omni-wheels. In at least one implementation, the omni-wheels are passive omni-wheels configured to roll along the longitudinal direction of the pipeline while maintaining contact with the pipe 135. The use of omni-wheels allows the inspection crawler 102 to accommodate a range of different pipeline diameters compared with conventional wheels. In one or more alternative embodiments, the rolling elements 130 are conventional wheels configured to roll along the longitudinal direction of the pipeline while maintaining contact with the pipe 135. In at least one alternative embodiment, the rolling elements 130 are actuated mecanum wheels that are configured to roll forward and sideways alone the pipeline. In an embodiment that utilizes mecanum wheels, by controlling the speeds of the crawler, the crawler can adjust its upward position on top of the pipe 135. In another alternative embodiment, the rolling elements are ball casters wheels that are configured to roll in any direction along the pipe 135.

The embodiment of FIGS. 3A and 3B shows latching arms 128 having omni-wheels. As the inspection crawler 102 moves along the pipeline, at least one pair of omni-wheels (e.g., the omni-wheels of opposing latching arms) are tensioned to maintain contact with the surface of the pipeline in at least one point (contact point) on each side of the pipe 135. In one particular embodiment, the angle between the contact points with the center of the pipe circumference is less than 180 degrees to ensure than the inspection crawler 102 does not detach from the pipe (see FIG. 3B). In at least one implementation, when the inspection crawler 102 is moving along a section of the underwater pipe in which the pipe is buried or substantial buried in the seabed, the latching arms 128 can be configured to unlatch from the surface of the pipe and roll (via rolling elements 130) on the seabed.

In one or more implementations, the latching arms 128 can be actuated using a pneumatic actuation mechanism.

Figure 4A:
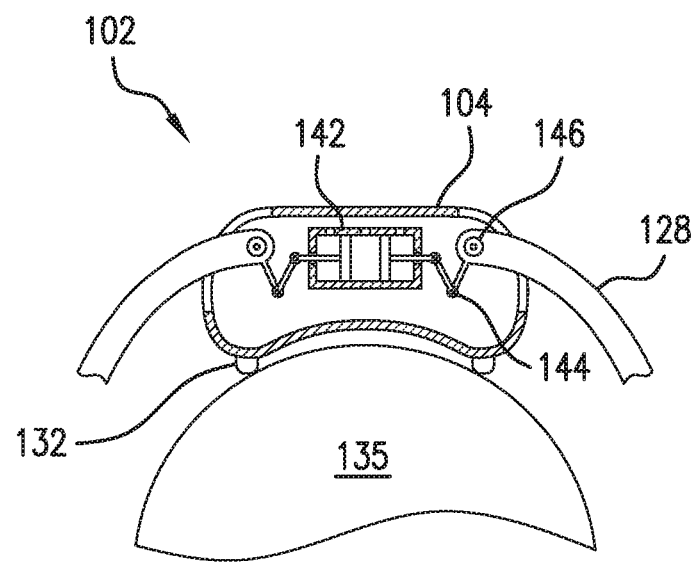
FIGS. 4A-C illustrate actuation mechanisms (4A, pneumatic actuation; 4B, electric actuation) of the latching arms of the underwater crawler and the connection of the latching arms to the spring-loaded active joint of the underwater crawler (4C) according to certain embodiments of the present application.

FIG. 4A shows an exemplary pneumatic actuation mechanism in accordance with one or more embodiments. The pneumatic actuation mechanism can be controlled by the processor 112 executing one or more software modules 118, including latching module 124. As shown in FIG. 4A, the pneumatic actuation mechanism includes a dual pneumatic actuator 142 for each pair of latching arms 128, the actuator 142 being operatively connected to the housing 104 and the latching arms 128. More specifically, the pneumatic actuation mechanism further comprises a crank piston 144 for each latching arm connected to the pneumatic actuator 142, and a rotational joint 146 connecting the crank piston 144 to the latching arm 128. Using the pneumatic actuation mechanism, the latching arms of the crawler are configured to selectively hug the surface of the pipe 135 (via the rolling elements 130) and detach from the surface. The pneumatic actuation mechanism can be advantageous in that it provides both actuation force and spring-like elasticity. The actuation force and spring-like elasticity of the pneumatic actuation mechanism allows the latching arms to accommodate for irregularities in the concrete surface of the pipe. Further, in embodiments in which the pneumatic actuation mechanism is used with latching arms having omni-wheels, the omni-wheels allow for friction-less motion in both longitudinal and circumferential directions and enable attachment for different pipe diameters.

Figure 4B:
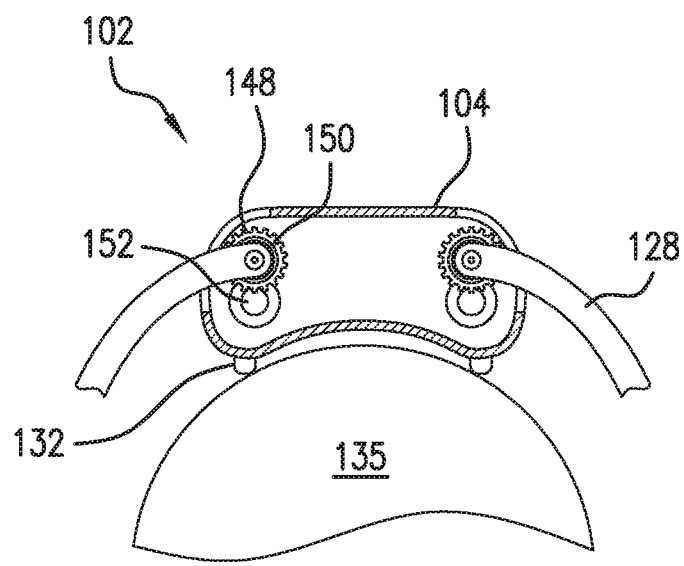

In at least one implementation, the latching arms can be actuated using an electric actuation mechanism. FIG. 4B shows an exemplary electric actuation mechanism in accordance with one or more embodiments. The electric actuation mechanism can be controlled by the processor executing one or more software modules 118, including latching module 124. As shown in FIG. 4B, the electric actuation mechanism includes a pinion gear 148 for each latching arm 128, the pinion gears 148 being operatively connected to the housing 104. The electric actuation mechanism further comprises a torsion spring 150 and a worm gear motor mechanism 152 for each latching arm, both the torsion spring 150 and the worm gear motor mechanism 152 being operatively connected to the pinion gear 148 for each latching arm 128. In at least one implementation featuring the electric actuation mechanism, the latching arms 128 use the torsion spring 150 to maintain tension while hugging the pipe 135 (e.g., via rolling elements 130). The electric actuator mechanism configures the latching arms to selectively hug onto the surface of the pipe 135 and retract from the surface of the pipe 135. In a particular implementation, the worm gear motor mechanism 152 is configured to hold the latching arm in tension without consuming power. As such, in this implementation, power is only needed during attaching (hugging) and detaching of the latching arm from the surface of the pipe 135.

Figure 4C:
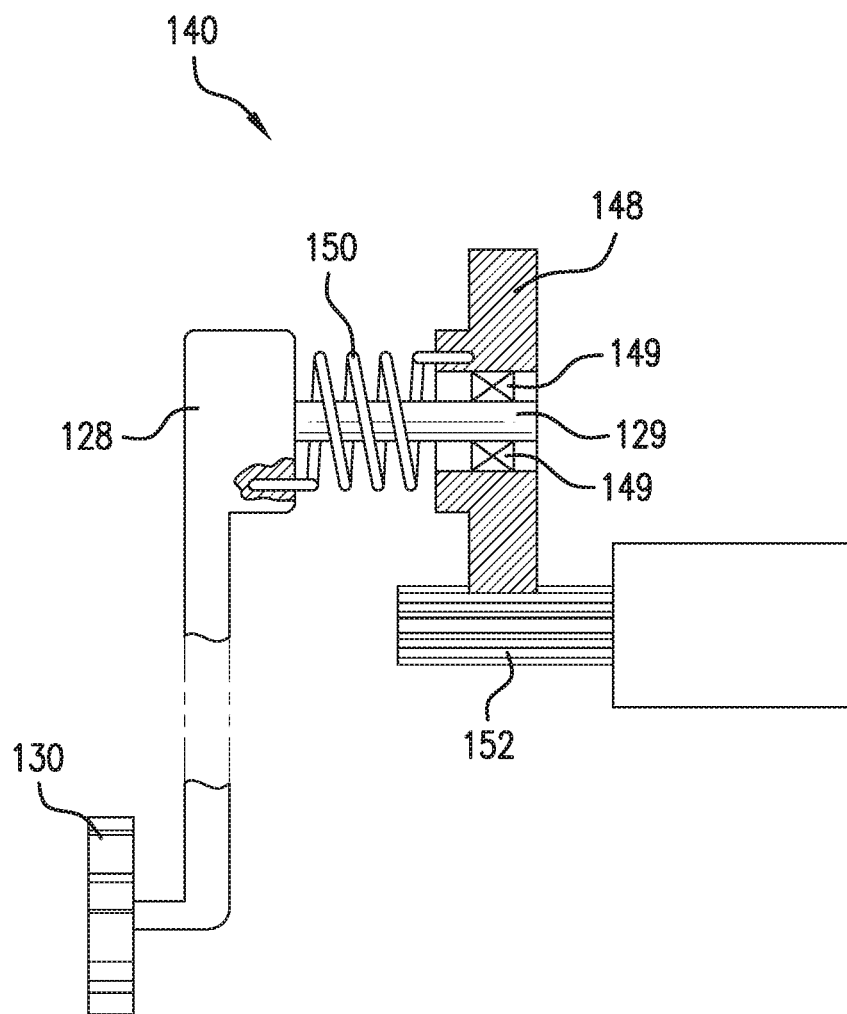

FIG. 4C illustrates the components of the spring-loaded active joint 140 of the inspection crawler 102 according to one or more embodiments. As discussed above, each latching arm 128 can be operatively connected to the housing 104 of the inspection crawler 102 via a spring-loaded active joint 140. As shown in FIG. 4C, in one or more implementations the spring-loaded active joint 140 can comprise a pinion gear 148 having a bearing 149, a torsion spring 150 arranged between the latching arm 128 and the pinion gear 148, and worm gear motor mechanism 152. The latching arm 128 can include a shaft 129 that is rigidly coupled to the latching arm and is configured for attachment to the active joint 140. As shown in FIG. 4C, in at least one embodiment the shaft 129 is freely rotating and its distal end is arranged within the bearing 149 of the pinion gear 148. The motor of the worm gear motor mechanism 152 rotates the worm gear which in turn rotates the pinion gear 148 that houses in it the freely rotating shaft 129. When the pinion gear 148 is rotated it winds the torsion spring 150 which rotates the latching arm 128 and provides elasticity to its rotation.

Figure 5A:
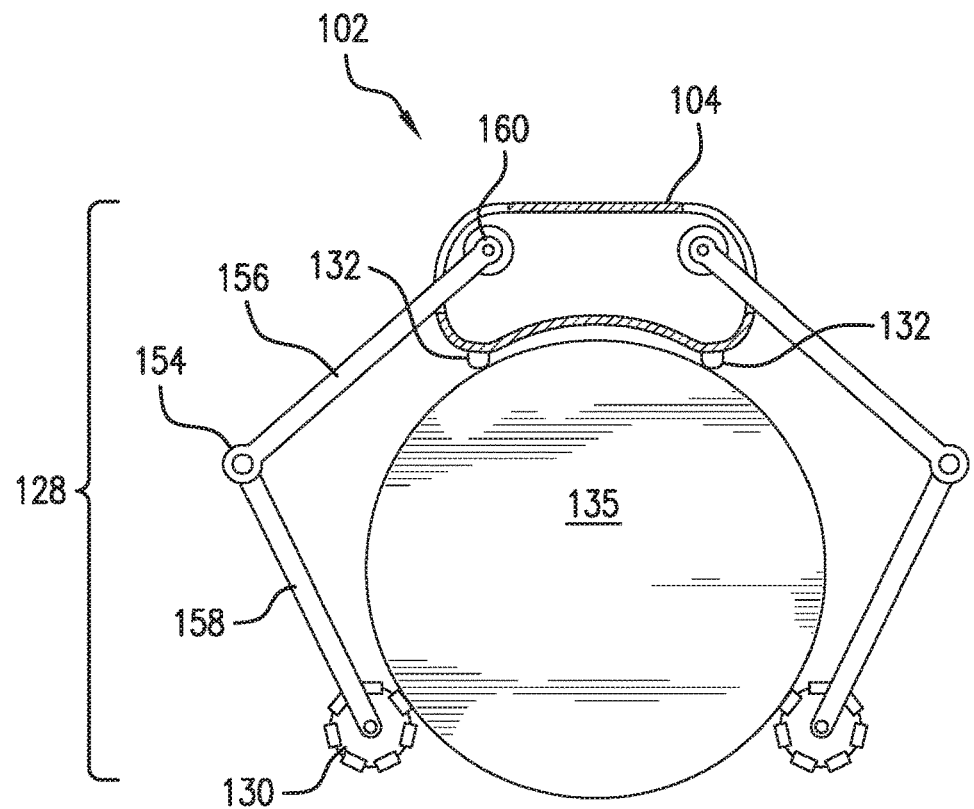
FIGS. 5A-B illustrate an alternative configuration of the underwater crawler and its attachment to an underwater pipeline according to at least one embodiment of the present application.
Figure 5B:
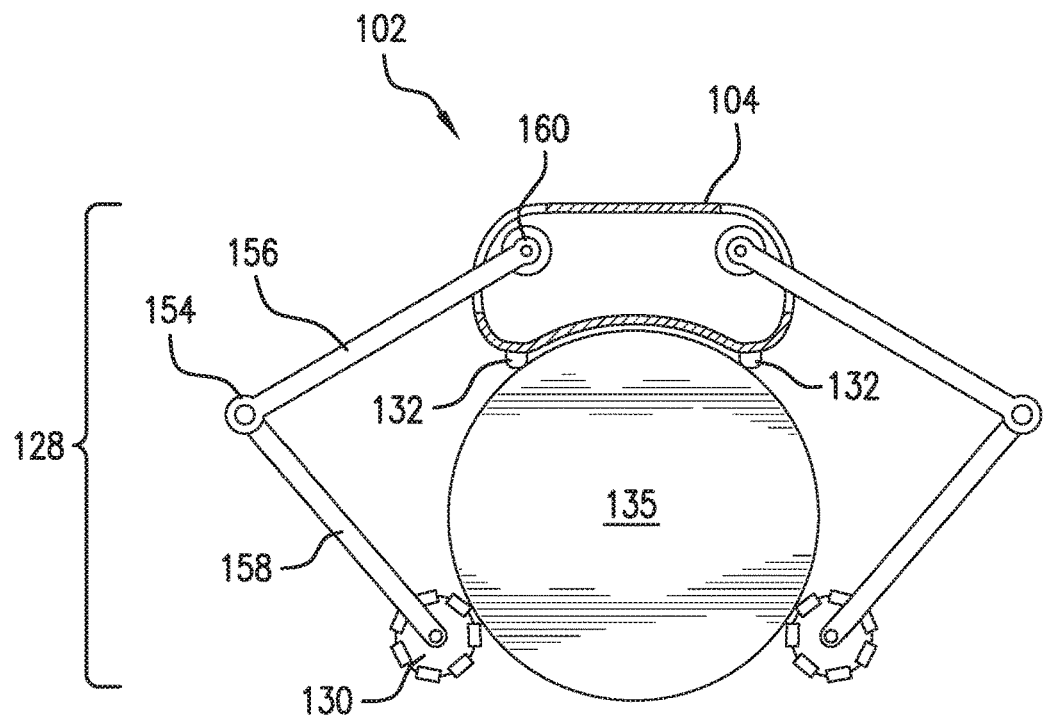

With reference to FIGS. 5A and 5B, in one or more alternative implementations, the latching arms 128 can comprise a joint 154. As shown in FIGS. 5A and 5B, the joint 154 divides the latching arm 128 into an upper segment 156 and a lower segment 158. The addition of a joint 154 to the latching arm provide the latching arm with two degrees of freedom and thus allows the inspection crawler 102 to easily adjust to pipes of different circumferences by adjusting the effective length of the latching arm 128. For instance, in FIG. 5A, the latching arm 128 having the joint 154 is able to traverse a pipe having a relatively large circumference, and FIG. 5B, the same latching arm 128 can accommodate a pipe having a much smaller circumference by shortening the effective length of the latching arms 128. In one or more implementations, the effective length of the latching arms 128 can be adjusted in a rotational manner. For example, FIGS. 5A and 5B show a rotational connection 160 between the upper segment 156 and the housing of the inspection crawler. Rotation of the latching arm 128 via the rotational connection 160 results in the lengthening (FIG. 5A) or shortening (FIG. 5B) of the effective length of the latching arms 128 such that different pipe circumferences can be accommodated. As shown in FIGS. 5A-5B, the upper segment 156 can be attached to the housing 104 of the inspection crawler 102 via a translational connection, such that translation of the upper segment 156 results in the lengthening or shortening of the effective length of the latching arms 128.

Referring back to FIGS. 3A and 3B, in one or more embodiments, the inspection crawler 102 further comprises at least two pairs of driving wheels 132 attached to a bottom portion of the housing 104. In one or more implementations, the driving wheels 132 are configured to propel the inspection crawler 102 across the surface of the pipeline. In one or more embodiments, for each pair of driving wheels 132, one driving wheel is distributed on the left bottom portion of the inspection crawler 102 and one driving wheel is distributed on the right bottom portion of the inspection crawler 102. In one or more implementations, during movement of the inspection crawler 102 along the pipeline, at least the front-most and rear-most pairs of wheels are actuated to ensure that at least one pair of driving wheels is propelling the inspection crawler 102 at all times. This is particularly important when a pair of the wheels is crossing a weld joint 138 of the pipeline, as the pair of wheels that is crossing the weld joint 138 is not in contact with any surface, and thus cannot assist in propelling the inspection crawler 102. For instance, when the front-most pair of driving wheels is crossing a weld joint, at least the rear-most driving wheels are actuated and therefore propel the front-most pair of driving wheels (and the front portion of the crawler) across the weld joint. Conversely, when the rear-most pair of driving wheels is crossing a weld joint, at least the front-most driving wheels are actuated and therefore propel the rear-most pair of driving wheels (and the back portion of the crawler) across the weld joint.

In one or more alternative embodiments, the inspection crawler can comprise tread on the left and right sides of the crawler rather than driving wheels. In this embodiment, the tread length is preferably longer than the width of the weld joint, and the center of gravity of the crawler is substantially in the middle of the housing of the crawler to ensure the stability of the crawler. In one or more implementations, the tread length is at least twice as long as the width of the weld joint. In at least one implementation, the treads can be hinged on the outside of the crawler and tensioned to the circumference of the pipe.

With continued reference to FIG. 3A, in one or more embodiments, the inspection crawler 102 further comprises one or more inspection tools 134 operatively connected to the housing. In one or more embodiments, and as shown at FIG. 3A, the at least one inspection tool 134 can be an inspection arm (134) comprising an inspection probe 162 for visual inspection and/or collecting data related to the inspection of the underwater pipeline (e.g., weld joints of the pipeline). In this implementation, the inspection arm has adequate degrees of freedom to reach a 6 o'clock position for the inspection of a weld joint 138 along the underwater pipeline (see FIG. 3A). The length of the links of the inspection arm can be interchangeable and the selection of the right length can be based on the size of the pipe and its inspected weld joint. The movement of the inspection tools is controlled by the controller 110 via instructions implemented by the inspection module 126.

In at least one embodiment, the one or more inspection tools 134 can comprise an extendable probe operatively connected to the underside of the crawler 102. In this embodiment, the extendable probe can be configured to conduct spot checks at the 12 o'clock position on a weld joint. The extendable probe can be either actuated to deploy normally to the surface, or alternatively, can be passively mounted to the crawler through a suspension system.

Figure 5C:
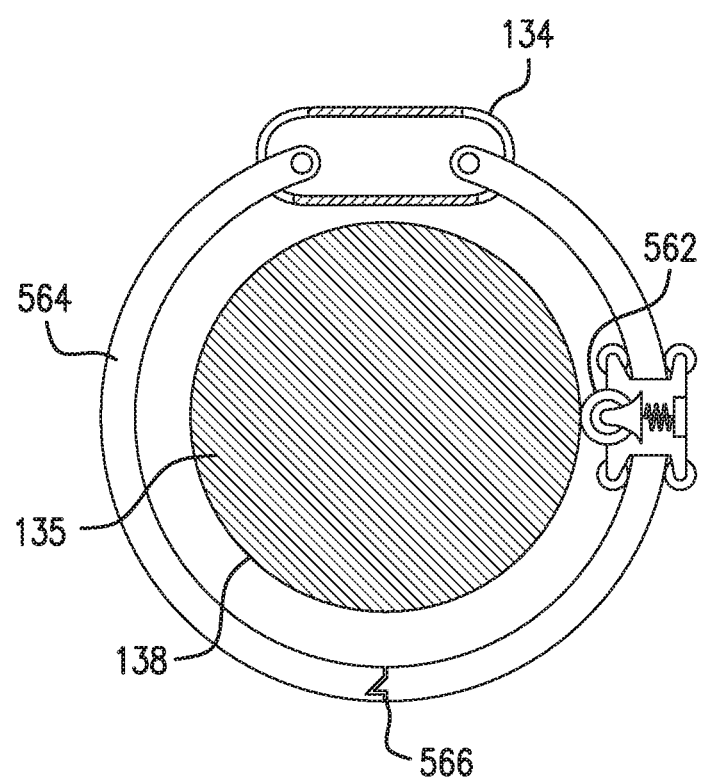
FIG. 5C illustrates an alternative implementation of an inspection tool of the underwater crawler according to at least one embodiment of the present application.

In one or more embodiments, the one or more inspection tools 134 can comprise a probe in the shape of a wheel that is configured to take cathodic protection (CP) and ultrasonic thickness (UT) measurements. In this embodiment, the probe is mounted on a ring that moves the probe around the circumference of the weld joint. In at least one implementation, as shown in FIG. 5C, the probe can be a wheel-shaped probe 562 (carried on a probe carrier having wheels, for example) that can be mounted on a circular rail/track 564 along which it can be rolled to acquire readings along the whole circumference of the weld joint 138 of the pipe 135. The rail 564 can be made of two semi-circles that are initially separated, and once a reading on the weld joint is needed, they are deployed to form a continuous track (e.g., via locking joint 566) for the wheel-shaped probe 562.

Figure 6A:
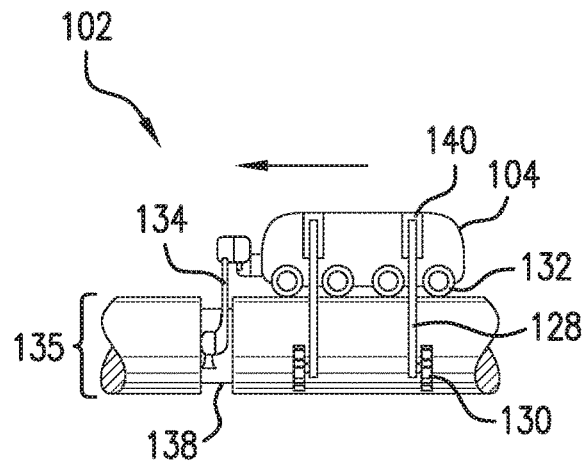
FIGS. 6A-D illustrate the movement of the underwater crawler across segments and a weld joint of the underwater pipeline according to at least one embodiment of the present application.

FIGS. 6A-6D illustrate the movement of the inspection crawler across segments and a weld joint 138 of the underwater pipeline according to at least one embodiment of the present application. FIGS. 6A-6D show a side view of the inspection crawler 102 in accordance with at least one embodiment. In this embodiment, the inspection crawler 102 comprises two pairs of latching arms 128, a front pair located proximate to the inspection arm 134, and a rear pair. As shown at FIG. 6A, as the inspection crawler 102 encounters a weld joint 138, the processor 112 executing one or more software modules 118, including driver module 122, configures the inspection crawler to stop or park at a location proximate to the weld joint 138. As shown in FIG. 6A, when the crawler 102 is parked, the at least rolling elements 130 of the latching arms 128 are pressed against the surface of the pipeline such that the rolling elements 130 of the front pair of latching arms are substantially aligned with the rolling elements 130 of the rear pair of latching arms. In certain embodiments, the inspection crawler 102 can be configured to inspect the weld joint 138 while the crawler 102 is parked (e.g., the processor 112 executing one or more software modules 118, including inspection module 126, configures the inspection tool 134 to inspect the weld joint 138).

Figure 6B:
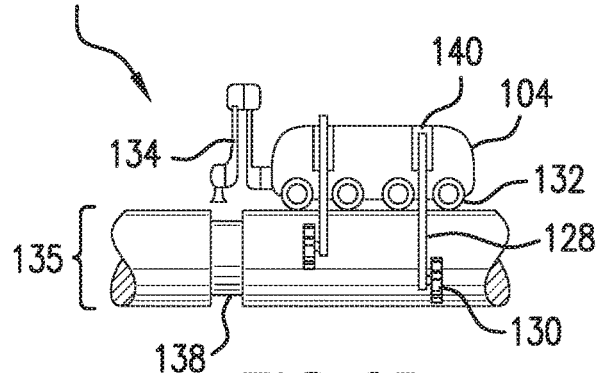

In accordance with the one or more embodiments shown FIGS. 6A-6D, in order for the inspection crawler 102 to traverse the weld joint 138, the processor 112 executing one or more software modules 118, including latching module 124, configures the inspection crawler to lift the rolling elements of the front pair of latching arms from the surface of the pipe 135. As shown in FIG. 6B, the rolling elements of the front pair of latching arms are lifted away from the surface of the pipe 135, while the rear pair of latching arms and their respective rolling elements remain in the same location as shown in FIG. 6A when the inspection crawler was "parked." After lifting the rolling elements of the front pair of latching arms, the inspection crawler is then configured to propel forward over the weld joint 138 via driving wheels 118 such that a front portion of the inspection crawler crosses the weld joint 138. In the embodiment of FIGS. 6A-6D in which the inspection crawler 102 comprises four sets of driving wheels, the front portion of the inspection vehicle generally corresponds to the portion of the crawler having the two front-most pairs of driving wheels, while the back portion of the crawler corresponds to the portion of the crawler having the two rear-most pairs of driving wheels.

Figure 6C:
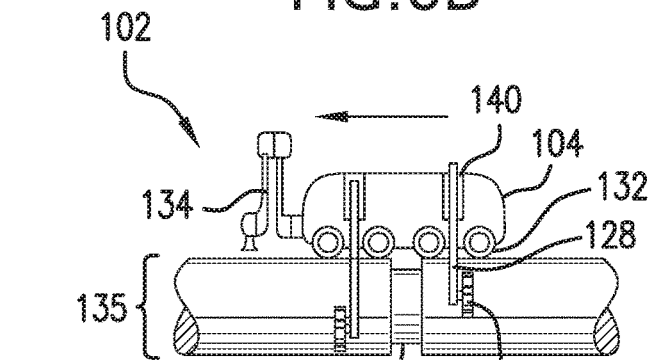
Figure 6D:
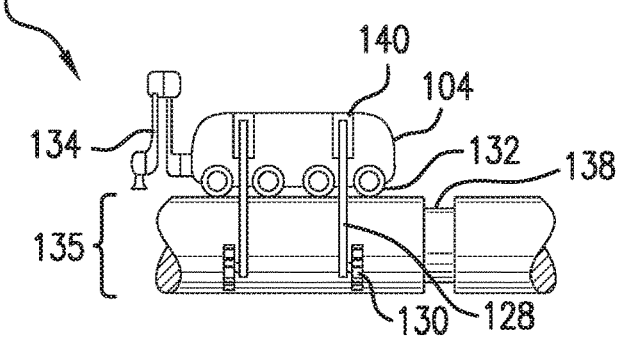

As shown in FIG. 6C, once the front portion of the inspection crawler 102 has crossed the weld joint 138, the crawler 102 is configured to lower the front pair of latching arms such that the rolling elements of the front pair of latching arms again contact the surface of the pipe 135. Further, the crawler 102 is configured to then lift the rear pair of latching arms such that the rolling elements of the rear pair of latching arms are not in contact with the surface of the pipe 135. In at least one implementation, the inspection crawler 102 stops in the middle of the weld joint during crossing in order to switch which latching arms are pressing against the pipe. In one or more embodiments, the inspection crawler 102 can continue to move across the weld joint as it switches which latching arms are pressing against the pipe so long as the switching of the latching arm is complete before the rear pair of wheels cross the weld joint. Once the rolling elements of the front pair of latching arms are contacting the pipe 135 and the rolling elements of the rear pair of latching arms have been lifted from the pipe 135, the inspection crawlers is configured to propel the remaining portion (back portion) of the crawler across the weld joint 138 via driving wheels 132. After the back portion of the crawler 102 has crossed the weld joint 138, the rear pair of latching arms is lowered such that the rolling elements of the rear pair of latching arms again contacts the surface of the pipe (see FIG. 6D). As such, once the crawler has completely crossed the weld joint, the crawler can be configured to continue to move along the pipeline with the rolling elements of both pairs of latching arms contacting and rolling along the surface of the pipe.

As mentioned above, in one or more implementations, when the front-most pair of driving wheels are crossing the weld joint, at least the rear-most driving wheels are actuated and therefore propel the front-most pair of driving wheels (and the front portion of the crawler) across the weld joint. Conversely, when the rear-most pair of driving wheels is crossing a weld joint, at least the front-most driving wheels are actuated and therefore propel the rear-most pair of driving wheels (and the back portion of the crawler) across the weld joint.

Figure 7A:
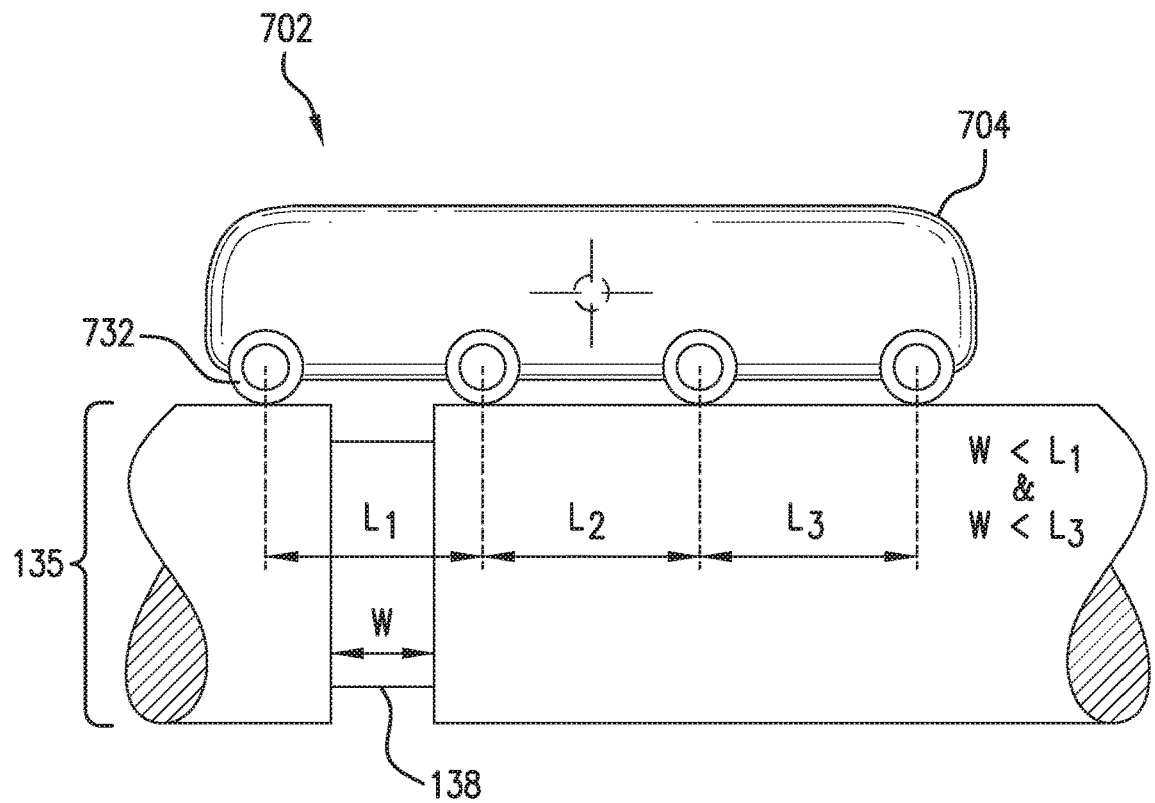
FIGS. 7A-C illustrate another embodiment of the underwater crawler having four pairs driving wheels and its movement across segments and a weld joint of the underwater pipeline according to at least one implementation of the present application.
Figure 7B:
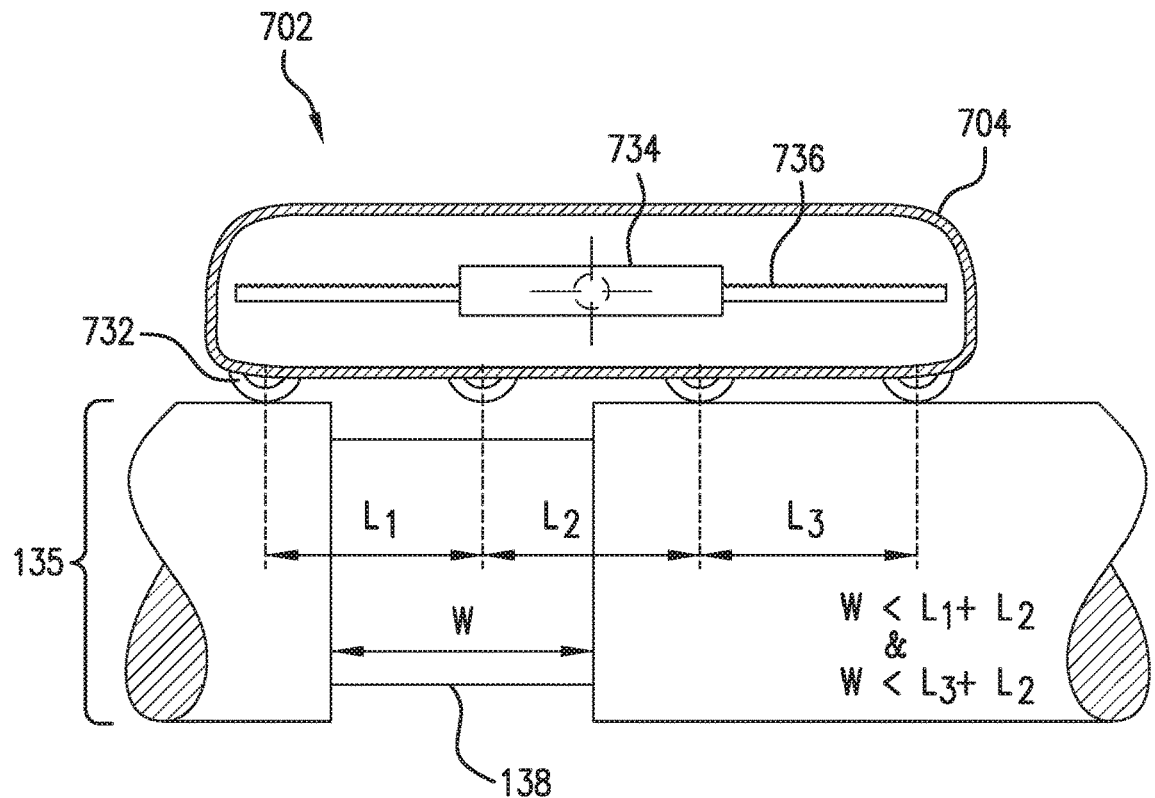
Figure 7C:
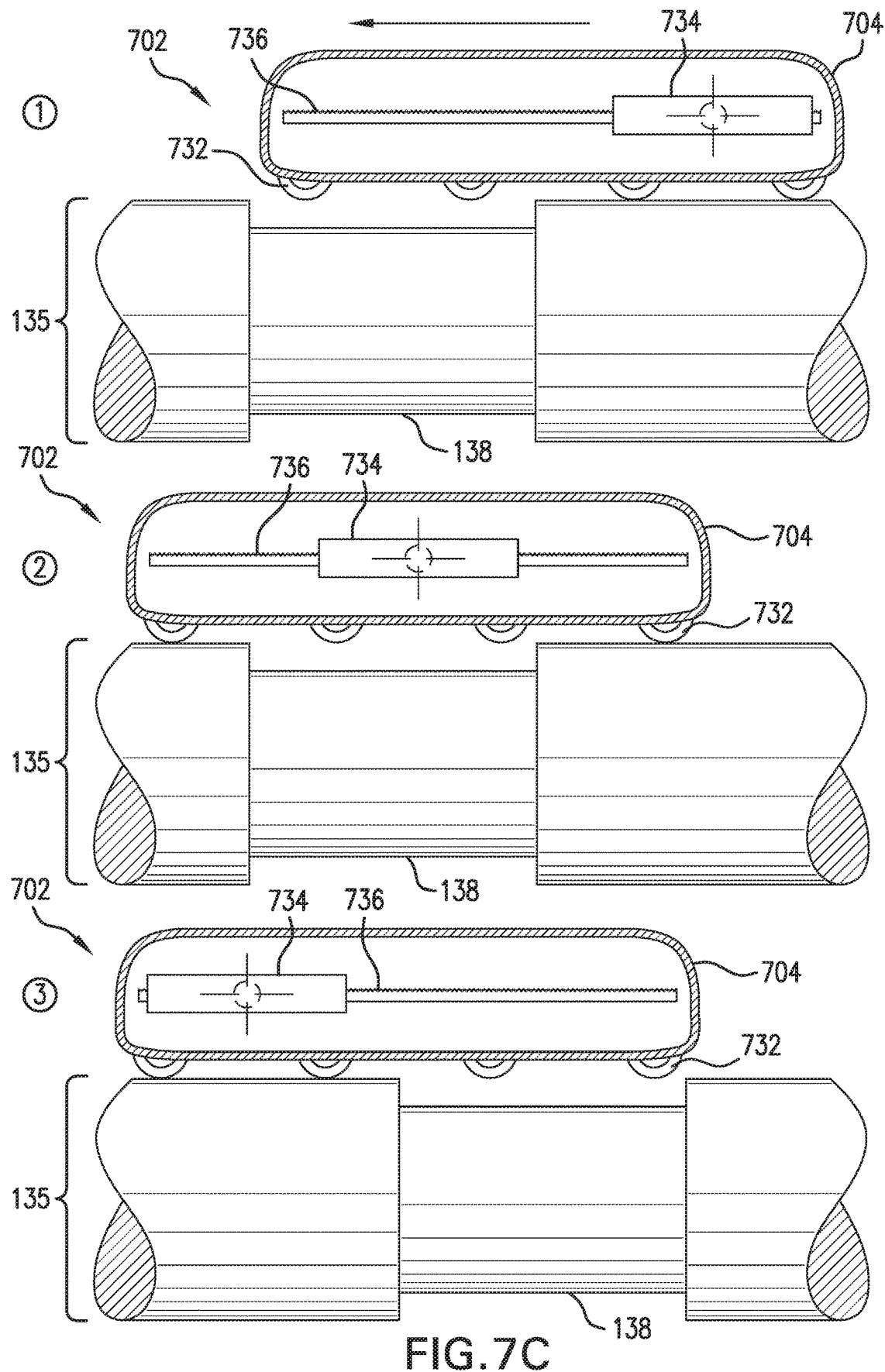

FIGS. 7A-7C illustrate side views of the underwater crawler of the present application according to an alternative embodiment similar to the ones discussed above. Accordingly, similar parts share a similar numbering convention, except that a "7" prefix is used instead of a "1" prefix. As exemplified in FIG. 7A, in this embodiment, the inspection crawler 702 comprises a housing 704. While not shown in the figures, the housing 704 can feature substantially the same components as shown in the housing 104 of FIG. 1, such as a power source, a controller, and a processor. Further, in at least one embodiment, the housing can further including at least one inspection tool that is operatively connected to the housing. Like the previous embodiments, the crawler 702 can also include at least two pairs of driving wheels 732 attached to the bottom surface of the housing 704 configured to propel the inspection crawler across a surface of the pipeline. As show in FIG. 7A, in at least one implementation, the crawler 702 can include four pairs of driving wheels 732 attached to the bottom surface of the housing 704. In this embodiment, the center of gravity of the crawler 702 is located substantially in the center of the crawler. In one or more implementations, and as shown in FIG. 7A, the center of gravity is located between the middle pairs of driving wheels 732.

With continued reference to FIG. 7A, in at least one implementation, the length between the front pair of driving wheels and the adjacent pair of wheels ($L_1$), and the length between the rear pair of driving wheels and its adjacent pair of wheels ($L_3$) are each longer than the width (W) of the weld joints of the pipeline the inspection crawler is moving along. As discussed above with regards to the first embodiment, when the inspection crawler 702 is in motion, at least the front pair and rear pair of driving wheels are activated and thus propel the crawler along the pipe 135. As such, having an $L_1$ that is greater than W helps to prevent the front pair of driving wheels—a propelling force of the crawler—from getting stuck in the weld joint 138 with its adjacent pair of driving wheels. Likewise, having an $L_3$ that is greater than W helps to prevent the rear pair of driving wheels—the other propelling force of the crawler—from getting stuck in the weld joint 138 with its adjacent pair of driving wheels. The length between the two innermost pairs of driving wheels ($L_2$) can be longer or shorter than W as long as the center of gravity is between the two innermost pairs of driving wheels.

With reference to FIGS. 7B-7C, in one or more implementations the center of gravity of the inspection crawler 702 is movable. As shown in FIG. 7B, a significant mass (moving mass) 734 of the crawler is located on a sliding rail 736 and movable along the sliding rail 736 in a horizontal direction. In one or more implementations, the significant mass 734 can comprises at least some of the internal components of the crawler, such as the battery, electronics, and/or ballast. In at least one embodiment, some or all of the significant mass 734 can be a separate weight. The movement of the significant mass 734 along the sliding rail 736 can be controlled by the processor 112 executing one or more software modules 118, including driver module 122. In some implementations of this embodiment (as shown in FIG. 7B), the sum of the length between the front pair of driving wheels and the adjacent pair of wheels ($L_1$) and the length between the two innermost pairs of driving wheels ($L_2$) (i.e., $L_1+L_2$) is longer than the width (W) of the weld joints of the pipeline. This spacing ensures that at least two of the four pairs of driving wheels are in contact with the surface of the pipe at all times.

FIG. 7C shows that as the inspection crawler 702 crosses an obstacle (e.g., weld joint 138), the significant mass 734 is configured to move to a location on the sliding rail such that the center of gravity prevents the crawler from getting stuck in the weld joint 138. In particular, as shown in drawing (1) of FIG. 7C, as the front portion of the inspection crawler 602 is parked at a location proximate to the weld joint and begins to cross the weld joint 138, the processor 112 executing one or more software modules 118, including driver module 122, configures the inspection crawler 702 to move or slide the significant mass 734 along the sliding rail to the rear portion (e.g., substantially at the rear end) of the crawler, such that the front portion of the crawler does not fall into the weld joint 138. As the front portion of the crawler 702 propelled over the weld joint (e.g., via driving wheels 732) and the front-most pair of driving wheels makes contact with the other side of the weld joint 138 (drawing (2) of FIG. 7C), the significant mass 734 is then configured to slide on the sliding rail to a location at the center or substantially at the center of the crawler 702, which, in the shown embodiment, is between the two innermost pairs of driving wheels. Finally, as center portion of the crawler 702 is propelled across the weld joint (e.g., via driving wheels 732) and the rear portion of the inspection crawler begins to cross the weld joint 138 (drawing (3) of FIG. 7C), the significant mass 734 is configured to slide on the sliding rail to a location in the front portion (e.g., substantially at the front end) of the crawler such that the rear portion of the crawler does not fall into the weld joint 138. Once the significant mass 734 is moved to the front portion of the crawler on the sliding rail, the rear portion of the crawler completes its crossing (e.g., is propelled via the driving wheels 732) over the weld joint. In one or more implementations, the significant mass 734 and the sliding rail 736 are located within the housing 704. In at least one implementation, the significant mass 734 and the sliding rail 736 are located on the outer surface of the housing 704.

Figure 8A:
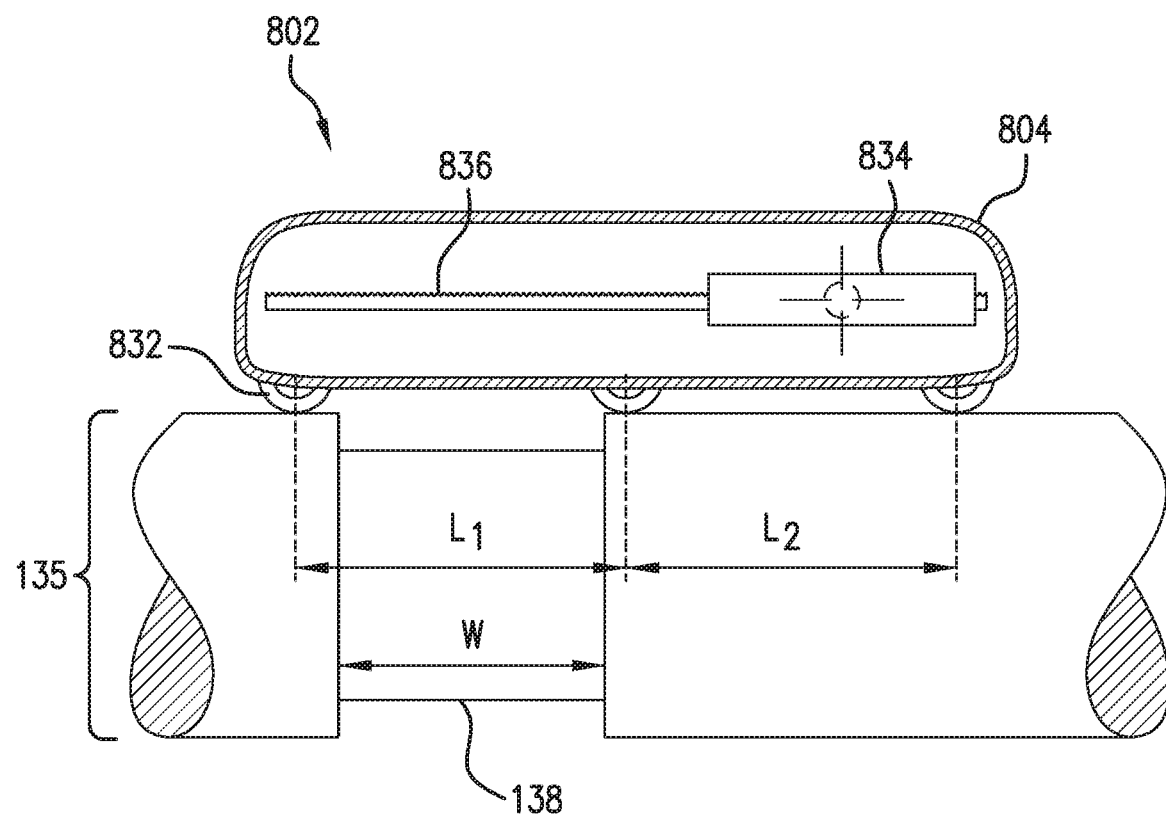
FIGS. 8A-B illustrate an embodiment of the underwater crawler having three pairs of driving wheels and its movement across segments and a weld joint of the underwater pipeline according to at least one embodiment of the present application.
Figure 8B:
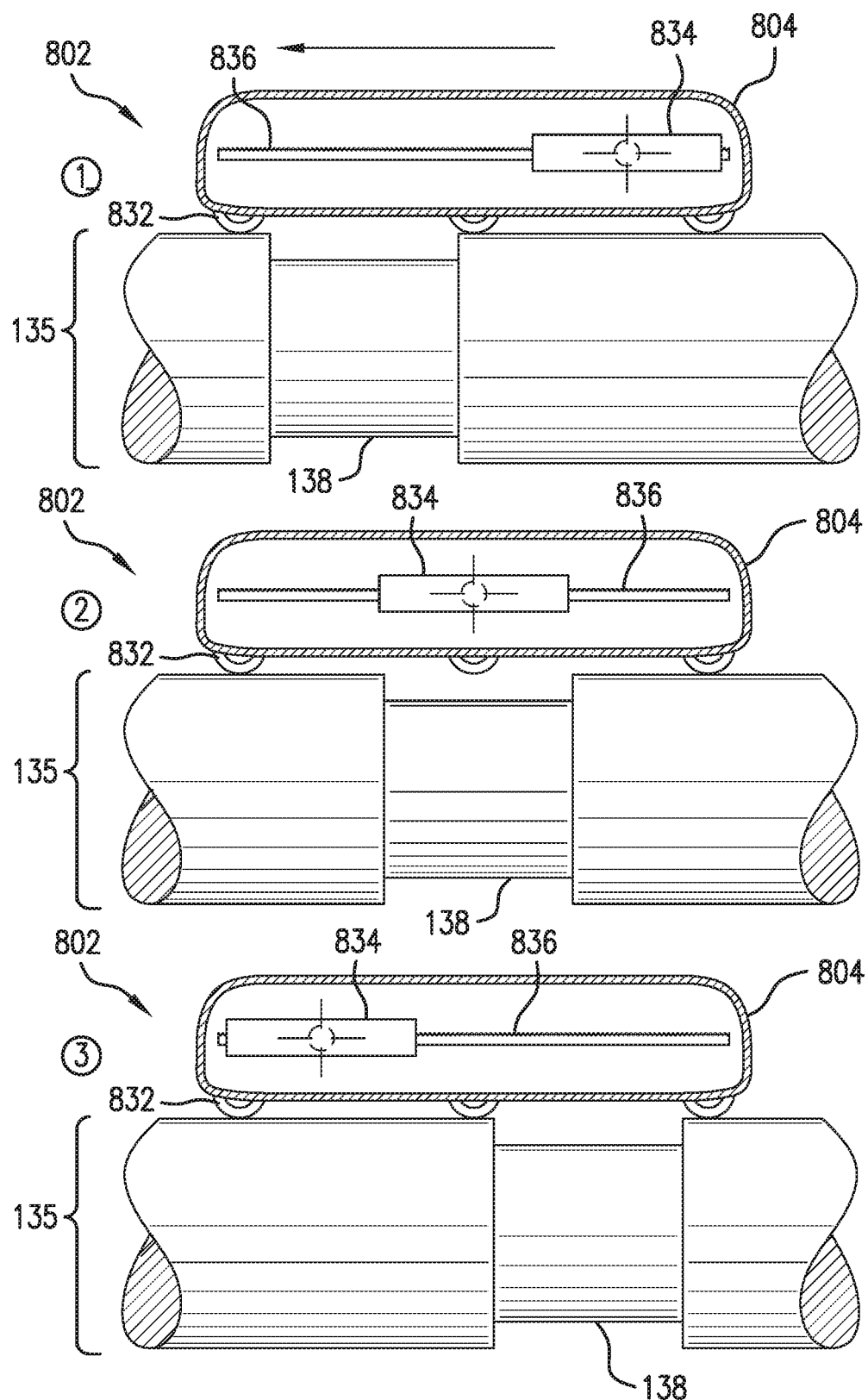

FIGS. 8A-8B shows another implementation of the inspection crawler having a movable center of gravity similar to that of FIGS. 7A-C. Accordingly, similar parts share a similar numbering convention, except that an "8" prefix is used instead of a "7" prefix. As shown in FIG. 8A, the crawler 802 having a housing 804 comprises three pairs of driving wheels 832 and a significant mass 834 located along a sliding rail 836. In this implementation, preferably, the length between the front pair of driving wheels and the middle pair of wheels ($L_1$), and the length between the rear pair of driving wheels and the middle pair of wheels ($L_2$) are longer than the width (W) of the weld joints of the pipeline the inspection crawler is moving along.

FIG. 8B shows how the inspection crawler 802 crosses a weld joint 138 of the pipeline. In this implementation, when crossing the weld joint 138, two pairs of driving wheels are in contact with the surface of the pipe 135 at all times, and the significant mass 834 is moved horizontally along the sliding rail 836 such that the center of gravity is between the two pairs of driving wheels currently in contact with the surface of the pipe 135. More specifically, as shown in drawing (1) of FIG. 8B, as the front pair of driving wheels crosses the weld joint 138, the significant mass 834 is configured to move along the sliding rail 836 to a position between the middle pair and rear pair of driving wheels, such that the front portion of the crawler does not fall into the weld joint 138. Once the front pair of driving wheels has crossed the weld joint 138 and the middle wheel begins to cross the weld joint 138 (drawing (2) of FIG. 8B), the significant mass 834 is configured to move along the sliding rail 836 to a position substantially in the center of the inspection crawler 802 (i.e., a position substantially aligned with the middle pair of driving wheels and in between the front and rear pairs of driving wheels). Finally, as shown in drawing (3) of FIG. 8B, as the rear pair of wheels begins to cross the weld joint 138, the significant mass 834 is configured to move along the sliding rail 836 to a position between the middle pair and front pair of driving wheels, such that the rear portion of the crawler does not fall into the weld joint 138.

Again, in one or more implementations, when the front-most pair of driving wheels are crossing the weld joint, at least the rear-most driving wheels are actuated and therefore propel the front-most pair of driving wheels (and the front portion of the crawler) across the weld joint. Conversely, when the rear-most pair of driving wheels cross a weld joint, at least the front-most driving wheels are actuated and therefore propel the rear-most pair of driving wheels (and the back portion of the crawler) across the weld joint.

Figure 9:
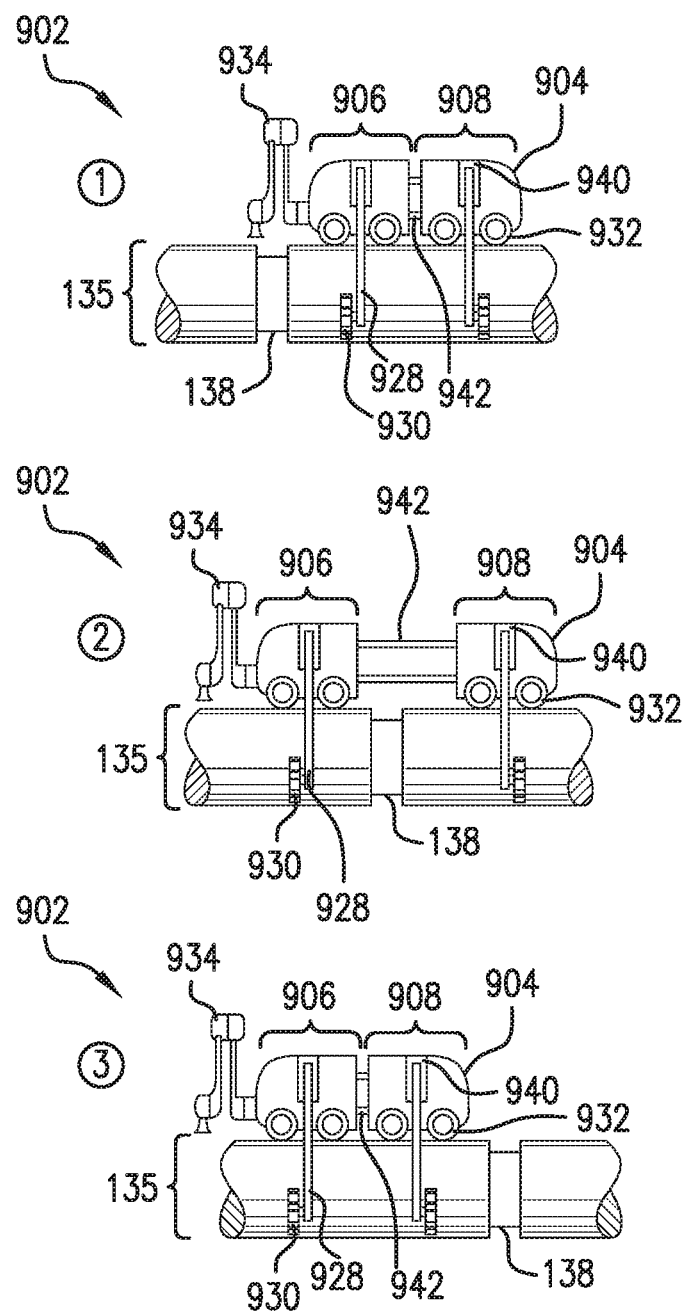
FIG. 9 illustrates another embodiment of the underwater crawler and its movement across segments and a weld joint of the underwater pipeline according to at least one embodiment of the present application.

FIG. 9 illustrates a side view of the underwater crawler of the present application according to still another embodiment similar to those embodiments discussed above. Accordingly, similar parts share a similar numbering convention, except that a "9" prefix is used. As shown in FIG. 9, in this embodiment, the inspection crawler 902 comprises a housing 904. While not shown in the figures, the housing 904 can feature substantially the same components as shown in the housing 104 of FIG. 1, such as a power source, a controller, and a processor. Like the previous embodiments, the crawler 902 can also include at least two pairs of driving wheels 932 attached to the bottom surface of the housing 904 configured to propel the inspection crawler across a surface of the pipeline. As show in FIG. 7A, in at least implementation, the crawler 902 can include a front portion 906 and a rear portion 908, two pairs of latching arms 928 each having rolling elements 930, four pairs of driving wheels 932 attached to the bottom surface of the housing 904, and an inspection tool 934. Each of the latching arms 928 are attached to the housing via a spring-loaded active joint 940. The inspection crawler 902 also comprises a pair of connecting structures 942 that connect the front portion 906 and rear portion 908 of the housing 904. The connecting structures 942 are mechanically rigid structures that connect the front portion 906 and rear portion 908, and actively adjusts the length of the crawler 902. In at least one implementation, the connecting structures 942 are extending linear actuators (as shown in FIG. 9). In alternative implementations, the linear actuators can be replaced with a rack and pinion mechanism, a pneumatic actuator, or another suitable power actuator.

The movement of the connecting structures 942 of the crawler 902 to adjust the length of the crawler 902 can be controlled via the processor 112 executing one or more software modules, including driver module 122. The ability to adjust the length of the crawler 902 allows the crawler 902 to cross weld joints in a "caterpillar-like" motion. For example, as shown at FIG. 9 (drawing 1), as the inspection crawler 902 encounters a weld joint 138, the inspection crawler is configured to stop or park at a location proximate to the weld joint 138. As shown, when the crawler 102 is parked, the at least rolling elements 930 of the latching arms 128 are pressed against the surface of the pipeline such that the rolling elements 930 of the front pair of latching arms are substantially aligned with the rolling elements 930 of the rear pair of latching arms. In certain embodiments, the inspection crawler 902 can be configured to inspect the weld joint 138 while the crawler 902 is parked. Further, as shown in drawing 2 of FIG. 9, after the crawler 902 parks at the weld joint 138, the processor 112 executing one or more software modules 118, including driver module 122, configures the inspection crawler 902 to extend the connecting structures 942 in a forward direction until the front portion 906 (first portion) of the housing 904 crosses the weld joint 138 (FIG. 9, drawings (1) and (2)). Once the front portion 906 of the housing 904 is across the weld joint 138, the crawler 902 is configured to contract the connection structures 942 such that the rear portion 908 (second portion) crosses the weld joint 138 while the crawler is stopped (FIG. 9, drawings (2) and (3)). In at least one implementation, the crossing of the rear portion 908 occurs when the crawler is stopped (e.g., brakes have been applied to the front driving wheels and the rolling elements of the front latching arms are pressed against the surface of the pipe).

The methods of movement of the inspection crawler are not limited to weld joints on a pipeline, but can also be applicable to other imperfections along the pipeline where the surface of the pipe is uneven. It should also be understood that while the above embodiments of the inspection crawler have been described above as moving in a forward direction along an underwater pipeline and over weld joints, in one or more embodiments the crawler can also move backwards along the pipe, including crossing over weld joints or other imperfections in a backward direction.

It should be understood that although much of the foregoing description has been directed to systems and methods for underwater inspection crawlers, the system and methods disclosed herein can be similarly deployed and/or implemented in scenarios, situations, and settings far beyond the referenced scenarios. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed:

1. A method for traversing a weld joint along a surface of an underwater pipeline with an inspection crawler having a housing, a power source, a controller, at least one inspection tool, at least two pairs of latching arms including a front pair and a rear pair, each latching arm having a rolling element, and at least two pairs of driving wheels, the method comprising:
   parking the inspection crawler at a location proximate to the weld joint, wherein the step of parking comprises pressing the rolling elements of the at least two pairs of latching arms against the surface of the pipeline such that the rolling elements of the front pair of latching arms are substantially aligned with the rolling elements of the rear pair of latching arms;
   lifting the rolling elements of the front pair of latching arms from the surface of the pipeline;
   propelling, using the driving wheels, a front portion of the inspection crawler across the weld joint;
   lowering the rolling elements of the front pair of latching arms to contact the surface of the pipeline and lifting the rolling elements of the rear pair of latching arms from the surface of the pipeline;
   propelling, using the driving wheels, a back portion of the inspection crawler across the weld joint; and
   lowering the rolling elements of the rear pair of latching arms to contact the surface of the pipeline.

2. A method for traversing a weld joint along a surface of an underwater pipeline with an inspection crawler having a front portion, a back portion, a connecting structure connecting the front portion and the back portion, wherein the connecting structure comprises an extendable and contractable member that is operable to elongate and shorten, respectively, a length of the inspection crawler, a power source, a controller, at least one inspection tool, at least two pairs of latching arms including a front pair and a rear pair, each latching arm having a rolling element, at least two pairs of driving wheels, and the method comprising:
   parking the inspection crawler at a location proximate to the weld joint, wherein the step of parking comprises pressing the rolling elements of the at least two pairs of latching arms against the surface of the pipeline such that the rolling elements of the front pair of latching arms are substantially aligned with the rolling elements of the rear pair of latching arms;
   extending the connecting structure to propel a first portion of the inspection crawler over the weld joint; and
   contracting the connecting structure to propel a second portion of the inspection crawler over the weld joint.

3. The method of claim 2, further comprising:
   inspecting the weld joint with the at least one inspection tool when the inspection crawler is parked.

4. The method of claim 2, wherein the connecting structure is an extending linear actuator.

5. The method of claim 2, wherein the inspection crawler comprises four pairs of driving wheels.

6. The method of claim 2, wherein the length of the inspection crawler is controlled via a processor included in the controller of the inspection crawler.

7. The method of claim 1, further comprising:
   inspecting the weld joint with the at least one inspection tool when the inspection crawler is parked.

8. The method of claim 1, wherein the inspection crawler comprises four pairs of driving wheels.

9. The method of claim 8, wherein the front portion of the inspection crawler comprises two pairs of driving wheels and the back portion of the inspection crawler comprises two pairs of driving wheels.

10. The method of claim 1, wherein the steps of lowering the rolling elements of the front pair of latching arms to contact the surface of the pipeline and lifting the rolling elements of the rear pair of latching arms from the surface of the pipeline occur when the inspection crawler is stopped.

11. The method of claim 1, wherein the steps of lowering the rolling elements of the front pair of latching arms to contact the surface of the pipeline and lifting the rolling elements of the rear pair of latching arms from the surface of the pipeline occur as the inspection crawler is moving across the weld joint.

* * * * *